US00PP20457P2

(12) United States Plant Patent
Bryant

(10) Patent No.: US PP20,457 P2
(45) Date of Patent: Nov. 3, 2009

(54) ***EPIPREMNUM* PLANT NAMED 'JADE SATIN'**

(50) Latin Name: *Epipremnum aureum*
Varietal Denomination: Jade Satin

(75) Inventor: Austin Theo Bryant, Zolfo Springs, FL (US)

(73) Assignee: Bryant Ag-Co, LLC, Zolfo Springs, FL (US)

( * ) Notice: Subject to any disclaimer, the term of this patent is extended or adjusted under 35 U.S.C. 154(b) by 0 days.

(21) Appl. No.: 12/156,093

(22) Filed: May 29, 2008

(51) Int. Cl.
*A01H 5/00* (2006.01)

(52) U.S. Cl. ..... Plt./373

(58) Field of Classification Search ..... Plt./373
See application file for complete search history.

*Primary Examiner*—Kent L Bell
(74) *Attorney, Agent, or Firm*—Jondle & Associates, P.C.

(57) ABSTRACT

A new *Epipremnum* (Pothos) plant particularly distinguished by thick robust stems, green leaves that are lightly mottled with a lighter green and cordate-shaped leaves with narrow to broadly acute apices, is disclosed.

1 Drawing Sheet

Genus and species: *Epipremnum aureum.*
Variety denomination: 'Jade Satin'.

BACKGROUND OF THE NEW PLANT

The present invention comprises a new and distinct cultivar of *Epipremnum* (also known as Pothos), botanically known as *Epipremnum aureum* and hereinafter referred to by the variety name 'Jade Satin'. The new variety originated as a naturally-occurring branch mutation of *Epipremnum* 'Silver Satin' (unpatented) in Zolfo Springs, Fla. in June 2007.

The new variety originated in Zolfo Springs, Fla. in June 2007 and has been asexually reproduced repeatedly by vegetative cuttings in Zolfo Springs, Fla. for over three generations. The present invention has been found to retain its distinctive characteristics through successive asexual propagations.

SUMMARY OF THE INVENTION

The following are the most outstanding and distinguishing characteristics of the new variety when grown under normal horticultural practices in Zolfo Springs, Fla.

1. Thick robust stems;
2. Green leaves that are lightly mottled with a lighter green; and
3. Cordate shaped leaves with narrow to broadly acute apices.

DESCRIPTION OF THE PHOTOGRAPHS

This new *Epripemnum* plant is illustrated by the accompanying photographs which show the overall plant habit and leaf color. The colors shown are as true as can be reasonably obtained by conventional photographic procedures. The photographs are of an 11-month-old plant taken in May 2008.

DESCRIPTION OF THE NEW VARIETY

Figure 1:
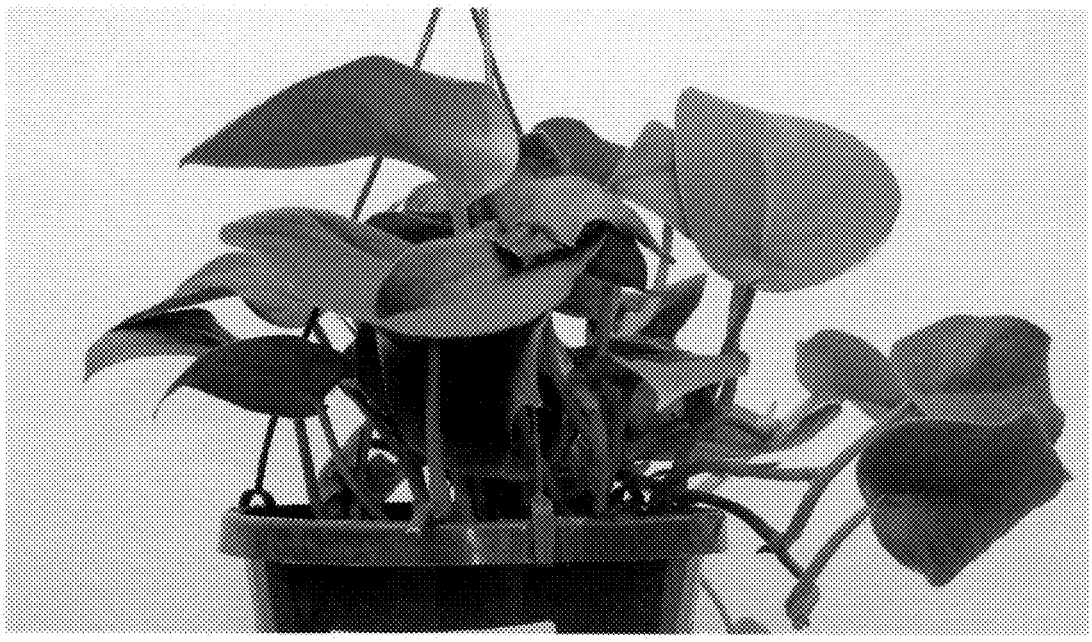
FIG. 1 shows the overall plant habit.
Figure 2:
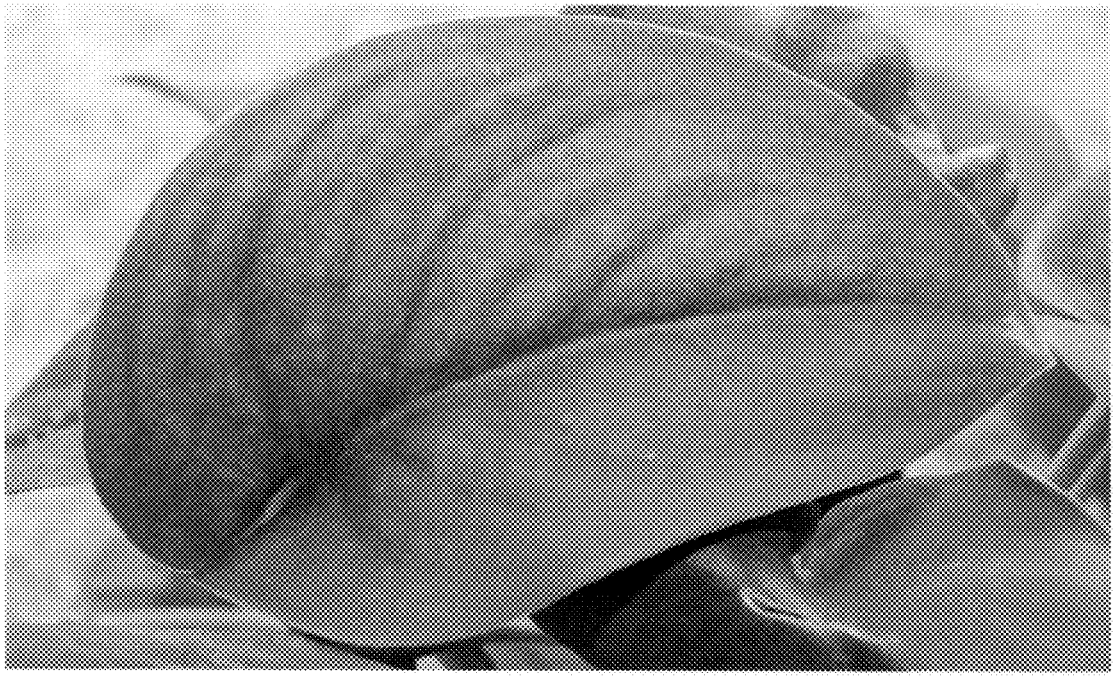
FIG. 2 shows a close up of the mature foliage.

The following detailed description sets forth the distinctive characteristics of 'Jade Satin'. The data which define these characteristics were collected from asexual reproductions carried out in Zolfo Springs, Fla. The plant history was taken on an 11-month-old plant in May 2008 in Fort Collins, Colo. Color readings were taken under natural light. Color references are primarily to The R.H.S. Colour Chart of The Royal Horticultural Society of London (R.H.S.) (2007).

DETAILED BOTANICAL DESCRIPTION

Classification:
- *Family.*—Araceae.
- *Botanical name.*—*Epipremnum aureum.*
- *Common name.*—Pothos, centipede tongavine.
- *Denomination.*—'Jade Satin'.

Plant:
- *Form.*—Vine.
- *Growth and branching habit.*—Prostrate or trailing stems rooting at the nodes, forming a compact mound when the stems are kept pruned back.
- *Height (from top of soil).*—15 cm to 20 cm; up to 20 m long if left un-pruned.
- *Width (horizontal plant diameter).*—About 30 cm to 40 cm.
- *Time to produce a finished plant.*—About 6 months to produce a finished 6-inch pot plant and about 8 months to produce a finished 8-inch pot plant.
- *Root description.*—Easily roots at the nodes; roots are thick, glabrous.
- *Propagation.*—By cuttings.

Stems:
- *Number of branches per plant.*—1 to 2.
- *Length (measured from surface of soil to tip).*—About 15 cm to 35 cm long; up to 20 m long if left un-pruned.
- *Width.*—0.4 cm to 0.6 cm.
- *Internode length.*—2.0 cm to 8.0 cm.
- *Color.*—RHS 144D for new growth, RHS 135A for old growth with RHS 191C spots or protuberances on the older growth.
- *Anthocyanin.*—Absent.
- *Texture.*—Smooth, glabrous.
- *Aspect.*—Trailing or prostrate.
- *Shape.*—Terete.
- *Strength.*—Robust, thick.

Leaves:

*Arrangement.*—Alternate.

*Immature leaf.*—Color: Upper surface: RHS 137B Lower surface: RHS 194B.

*Mature leaf.*—Color: Upper surface: RHS 139A and lightly mottled with RHS 137A Lower surface: RHS 191B.

*Length.*—8.0 cm to 15.0 cm.

*Width.*—4.0 cm to 10.0 cm.

*Shape.*—Cordate.

*Apex.*—Narrow to broadly acute.

*Base.*—Cordate.

*Margin.*—Entire.

*Texture.*—Adaxial and abaxial leaf surfaces are both thick while adaxial surface is also somewhat glossy.

*Pubescence* (*both surfaces*).—Glabrous.

*Venation pattern* (*both surfaces*).—Pinnate, with the veins following the outline of the leaf and the ends curved along the edge of the leaf margin.

*Venation color.*—Immature leaf: Upper surface: RHS 137B Lower surface: RHS 194B Mature leaf: Upper surface: RHS 139A Lower surface: RHS 191B.

Petioles:

*Aspect.*—Erect from trailing stem.

*Length.*—5.0 cm to 8.5 cm.

*Width.*—0.4 cm to 0.7 cm.

*Color.*—RHS 144D for new growth and 137B for older growth.

*Texture.*—Smooth, glossy, thick and glabrous.

Inflorescence: Not observed

Reproductive organs: Not observed

Fruit and seed set: None observed.

Disease and insect resistance: No particular susceptibility or resistance to pests or diseases noted.

COMPARISON WITH PARENTAL AND COMMERCIAL VARIETIES

'Jade Satin' differs from the parent 'Silver Satin' (unpatented) in that 'Jade Satin' has green leaves that are lightly mottled with a lighter green, while 'Silver Satin' has green leaves that are prominently mottled with greyed-green.

'Jade Satin' differs from the commercial variety 'Marble Queen' (unpatented) in that 'Jade Satin' has green leaves that are lightly mottled with a lighter green, while 'Marble Queen' has green leaves that are prominently mottled with white.

I claim:

1. A new and distinct cultivar of *Epipremnum* plant, as shown and described herein.

* * * * *